United States Patent
Fischer et al.

(10) Patent No.: US 10,893,695 B2
(45) Date of Patent: Jan. 19, 2021

(54) **PROBIOTIC BACTERIAL STRAIN OF *LACTOBACILLUS PLANTARUM* AND COMPOSITIONS AND USES THEREOF IN THE TREATMENT OF INFLAMMATION**

(71) Applicant: Probi AB, Lund (SE)

(72) Inventors: Jörg Thilo Fischer, Brakel (DE); Marcus Rudolf Götz, Oberweser (DE); Göran Molin, Lund (SE); Siv Ahrne, Lund (SE)

(73) Assignee: Probi AB, Lund (SE)

( * ) Notice: Subject to any disclaimer, the term of this patent is extended or adjusted under 35 U.S.C. 154(b) by 0 days.

(21) Appl. No.: 16/034,592

(22) Filed: Jul. 13, 2018

(65) Prior Publication Data

US 2019/0037902 A1 Feb. 7, 2019

Related U.S. Application Data

(63) Continuation of application No. PCT/EP2017/051003, filed on Jan. 18, 2017.

(30) Foreign Application Priority Data

Jan. 19, 2016 (GB) .................................. 1600975.5

(51) Int. Cl.
| | | |
|---|---|---|
| *A23L 33/135* | (2016.01) | |
| *A61K 8/99* | (2017.01) | |
| *A61K 35/747* | (2015.01) | |
| *C12R 1/25* | (2006.01) | |
| *C12N 11/04* | (2006.01) | |
| *C12N 1/20* | (2006.01) | |
| *A61P 1/02* | (2006.01) | |
| *A61Q 11/00* | (2006.01) | |
| *A61K 9/00* | (2006.01) | |
| *A23L 33/00* | (2016.01) | |

(52) U.S. Cl.
CPC .............. *A23L 33/135* (2016.08); *A23L 33/00* (2016.08); *A61K 8/99* (2013.01); *A61K 9/0063* (2013.01); *A61K 35/747* (2013.01); *A61P 1/02* (2018.01); *A61Q 11/00* (2013.01); *C12N 1/20* (2013.01); *C12N 11/04* (2013.01); *C12R 1/25* (2013.01); *A61K 2800/74* (2013.01)

(58) Field of Classification Search
CPC ........ A61K 35/747; C12N 11/04; C12R 1/25; A23L 33/135
See application file for complete search history.

(56) References Cited

U.S. PATENT DOCUMENTS

| | | |
|---|---|---|
| 4,518,615 A | 5/1985 | Cherukuri et al. |
| 5,093,136 A | 3/1992 | Panhorst et al. |
| 5,266,336 A | 11/1993 | McGrew et al. |
| 5,601,858 A | 2/1997 | Mansukhani et al. |
| 7,713,726 B2 | 5/2010 | Farmer |
| 2004/0101495 A1 | 5/2004 | Nase et al. |
| 2008/0241226 A1 | 10/2008 | Abeln et al. |
| 2008/0268006 A1 | 10/2008 | Molin et al. |
| 2009/0208469 A1 | 8/2009 | Alenfall et al. |
| 2010/0028449 A1 | 2/2010 | Prakash et al. |
| 2013/0209374 A1* | 8/2013 | Cune Castellana ...... A61K 8/99 424/48 |
| 2014/0023620 A1 | 1/2014 | Loudina |
| 2014/0065218 A1 | 3/2014 | Lang et al. |
| 2015/0238548 A1 | 8/2015 | Huang et al. |
| 2015/0240200 A1 | 8/2015 | Tsai et al. |
| 2015/0250834 A1 | 9/2015 | Tsai et al. |

FOREIGN PATENT DOCUMENTS

| | | |
|---|---|---|
| DE | 202009011379 U1 | 12/2010 |
| EP | 0242325 A2 | 10/1987 |
| EP | 1613740 A1 | 1/2006 |
| EP | 2420580 A1 | 2/2012 |
| JP | 2010-202557 A | 9/2010 |
| JP | 2014-000039 A | 1/2014 |
| RU | 2492851 C1 | 9/2013 |
| WO | 2000/20013 A1 | 4/2000 |
| WO | 2000/78322 A2 | 12/2000 |
| WO | 2010/008879 A2 | 1/2010 |
| WO | 2010/064373 A1 | 6/2010 |
| WO | 2010/077795 A2 | 7/2010 |
| WO | 2010/099824 A1 | 9/2010 |
| WO | 2012/022773 A1 | 2/2012 |
| WO | 2012/156491 A1 | 11/2012 |
| WO | 2014/140080 A1 | 9/2014 |
| WO | WO-2014140080 A1 * | 9/2014 ............ A23K 10/18 |

OTHER PUBLICATIONS

U.S. Appl. No. 16/070,553 (Year: 2018).*
https://en.wikipedia.org/wiki/Lactobacillus_plantarum, 2020 (Year: 2020).*
https://en.wikipedia.org/wiki/Lactobacillus, 2020 (Year: 2020).*
https://en.wikipedia.org/wiki/Lactic_acid_bacteria, 2020 (Year: 2020).*

(Continued)

*Primary Examiner* — Ruth A Davis

(74) *Attorney, Agent, or Firm* — McCarter & English, LLP; Yu Lu

(57) ABSTRACT

The present invention relates to a novel bacterial strain, *L. plantarum* GOS 42 (DSM 32131), isolated preparations and compositions thereof; and their use in medicine, especially in the treatment and/or prevention of inflammation.

13 Claims, 4 Drawing Sheets

(56) References Cited

OTHER PUBLICATIONS https://en.wikipedia.org/wiki/Probiotic, 2020 (Year: 2020).*
BioGrowing, Typical Biotic Health™ supplements. Biogrowing probiotics brochure. Retrieved online at: http://www.slideshare.net/AllenLI12/biogrowing-probiotics-brochure-49535320. 1 page, (2015).
Biotic Health™, Dietary Supplements (Biotic Health™). Retrieved online at: http://office.biogrowing.com/en/Tech.asp. 3 pages, (2007-2010).
IQBAL et al., beta-Galactosidase from Lactobacillus plantarum WCFS1: biochemical characterization and formation of prebiotic galacto-oligosaccharides. Carbohydr Res. Jul. 2, 2010;345(10):1408-16.
Snel et al., Competitive selection of lactic acid bacteria that persist in the human oral cavity. Appl Environ Microbiol. Dec. 2011;77(23):8445-50.

* cited by examiner

PROBIOTIC BACTERIAL STRAIN OF *LACTOBACILLUS PLANTARUM* AND COMPOSITIONS AND USES THEREOF IN THE TREATMENT OF INFLAMMATION

REFERENCE TO RELATED APPLICATIONS

This application is a continuation of International Patent Application No. PCT/EP2017/051003, filed on Jan. 18, 2017, which claims priority to GB 1600975.5, filed on Jan. 19, 2016. The entire contents of each of the above-referenced applications, including any drawings, are incorporated herein by reference.

DETAILED DESCRIPTION OF THE INVENTION

Figure 1A:
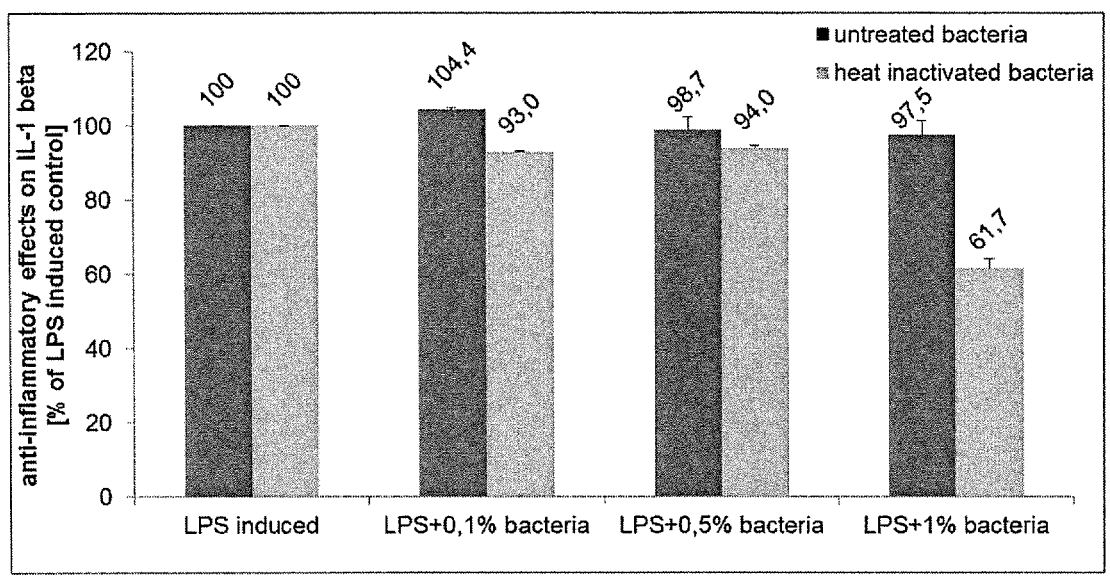
FIGS. 1A-1F show the anti-Inflammatory effects of *Lactobacillus plantarum* GOS 42 (DSM 32131) in human primary monocytes on interleukin 1 beta (FIG. 1A), interleukin 6 (FIG. 1B), interleukin 8 (FIG. 1C), prostaglandin E2 (FIG. 1D), tumor necrosis factor alpha (FIG. 1E) and isoprostane (FIG. 1F). The left column refers to untreated cells, the right column to attenuated cells.
Figure 1B:
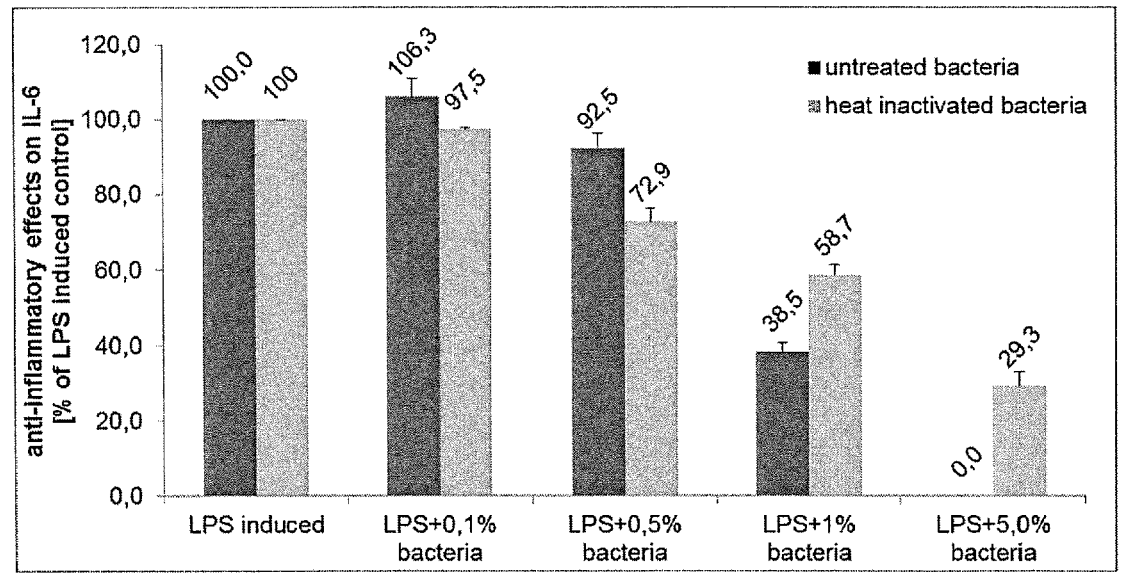
Figure 1C:
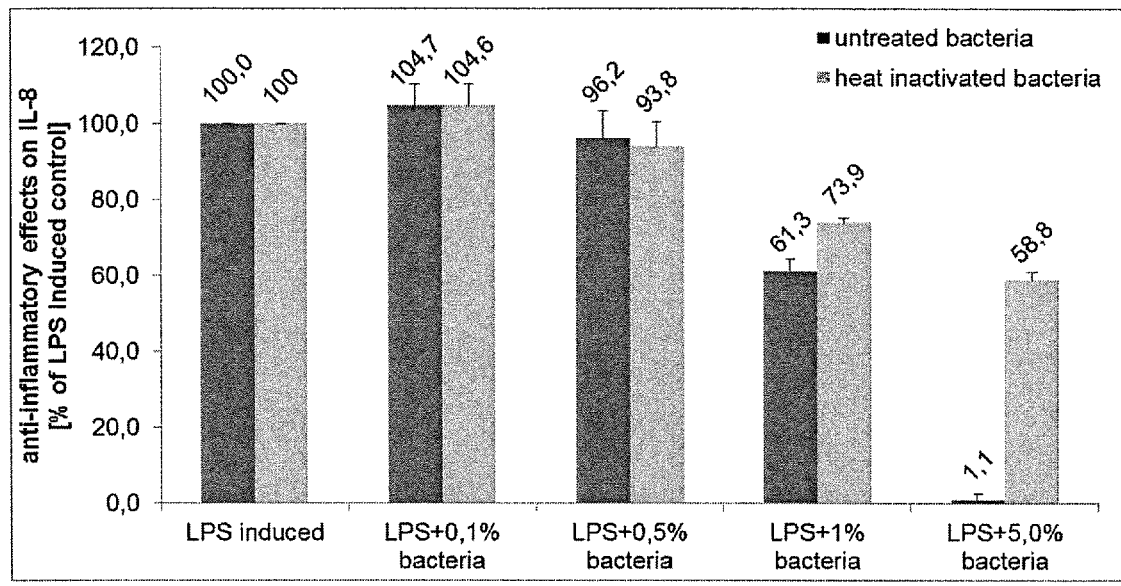
Figure 1D:
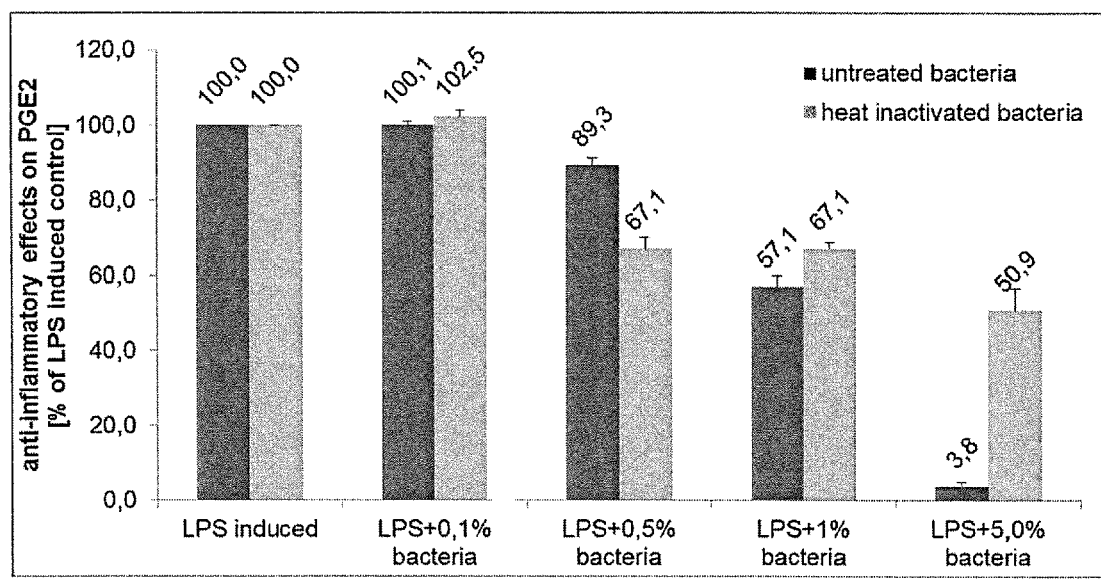
Figure 1E:
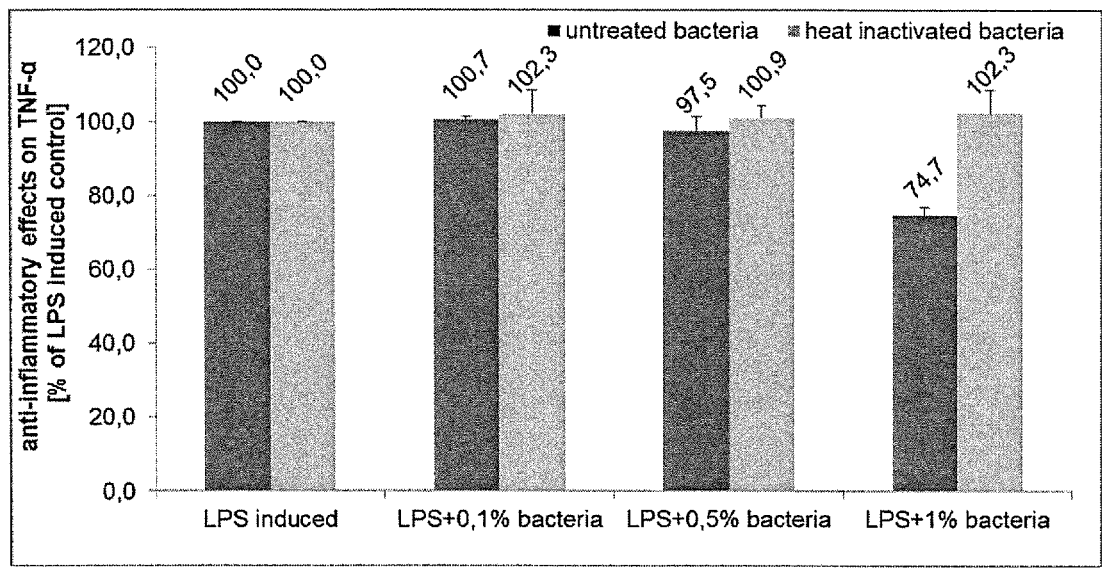
Figure 1F:
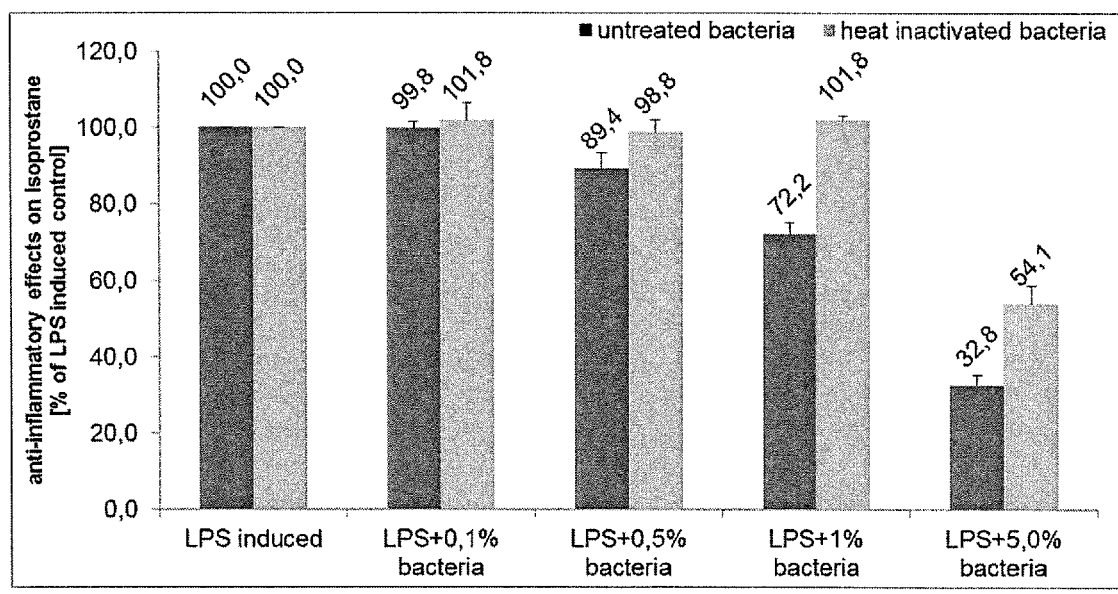

The present invention relates to a novel bacterial strain *Lactobacillus plantarum* Gos 42 (DSM 32131), and compositions thereof for use as a probiotic. The novel strain has particular use in medicine, especially in the treatment and/or prevention of inflammation. The novel strain and compositions thereof find particular utility in the treatment and/or prevention of inflammation in the oral cavity, preferably for the treatment and/or prevention of gingivitis and/or peridontitis.

In particular, the novel strain and compositions thereof can be used as anti-inflammatory agents for reducing or inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-κB.

Preferably the novel strain of the invention is a probiotic, that is, a microoganism which confers a benefit when grown in a particular microenvironment by, e.g. inhibiting or preventing the growth of other organisms within the same microenvironment. Examples of probiotic microorganisms include Lactobacilli which can colonise the gastrointestinal tract, at least temporarily, to displace or destroy pathogenic organisms, as well as providing other benefits to the host.

As utilized herein, "probiotic" refers to microorganisms that form at least a part of the transient or endogenous flora and thereby exhibit a beneficial prophylactic and/or therapeutic effect on the host organism. Probiotics are generally known to be clinically safe (i.e., non-pathogenic) by those individuals skilled in the art. By way of example, and not of limitation to any particular mechanism, the prophylactic and/or therapeutic effect of an acid-producing bacteria of the present invention results, in part, from a competitive inhibition of the growth of pathogens due to: (i) their superior colonization abilities; (ii) parasitism of undesirable microoganisms; (iii) the production of acid (e.g., lactic, acetic, and other acidic compounds) and/or other extracellular products possessing anti-microbial activity; and (iv) various combinations thereof. It should be noted that the aforementioned products and activities of the acid-producing bacteria of the present invention act synergistically to produce the beneficial probiotic effect disclosed herein.

By purified or isolated preparation of a bacterial strain is meant that the preparation does not contain another bacterial species or strain in a quantity sufficient to interfere with the replication of the preparation at a particular temperature. A purified or isolated preparation of a bacterial strain is made using standard methods, e.g. plating at limiting dilution and temperature selection.

Inflammatory conditions of the gums are primarily induced by the formation of dental plaque. Colonizing bacteria form a biofilm on the surface of the teeth aided by the presence of food residues as well as components of saliva. If not sufficiently cleared away at an early stage, plaque films on the surface of the teeth result in deposition of dental calculus which is very hard to remove. The presence of raised numbers of bacteria at the gingival margin leads to inflammation of the gingivae, known as gingivitis. In susceptible individuals, gingivitis may progress to periodontitis, which can lead to tooth loss. In particular, lipopolysaccharides (LPS) present in Gram-negative bacteria can cause a non-specific immune response by LPS-stimulated macrophages, which release prostaglandin E2 (PEG2) and pro-inflammatory mediators such as interleukins and TNF-α in the affected tissue. The pro-inflammatory mediators induce the release of further PGE2s and matrix metalloproteinases (MMPs) from the residing fibroblasts, which destroy the extracellular matrix of the surrounding tissue. This allows bacteria to penetrate deeper into the tissue and promote the inflammatory process independent of the outer layer of the epithelium and the dental root causing the formation of a periodontal pocket. The alveolar bone supporting the tooth resorbs ahead of the advancing bacteria and, causing the tooth to become unstable and, if left untreated, lost.

In order to avoid progressive destruction of the gums, inflammatory responses in the oral cavity need to be suppressed in the early stages or ideally prevented.

Many different approaches have addressed this problem, ranging from improved methods for the mechanical removal of plaque to the use of oral care products with strong anti-bacterial properties.

However, not all the bacteria present in the oral cavity are disease-associated and many even promote oral health. Therefore, it is desirable to establish a balance towards a healthy composition of the mouth microbiota instead of non-specifically eradicating resident bacteria.

The normal oral microbiota is highly complex and includes over 700 bacterial species as well as archaea, fungi, protozoa and viruses. Lower gum commensals such as lactobacilli and bifidobacteria have been shown to have beneficial effects on gut health, including some anti-inflammatory properties, when administered as probiotics.

Probiotic action of bacteria in the oral cavity has been subject to some research but results vary strongly with the species used and suitable parameters for efficient application are hard to establish because the action may rely on largely unrelated effects.

Among the probiotic actions, general anti-bacterial effects against disease-associated species, the reduction or prevention of bacterial adhesion to the surface of the teeth as well as anti-inflammatory effects have been discussed in the literature.

However, little is known about the influence of specific probiotic strains on inflammatory mechanisms, in particular with respect to the suppression of different inflammatory mediators. Remarkably, it has been found out in the extensive investigations leading up to the present invention, that some strains of generally acknowledged probiotic bacteria may also enhance the release of pro-inflammatory factors at certain doses. Hence, there remains an unmet need for novel strains which exhibit desirable effect on pro-inflammatory and anti-inflammatory mediators of inflammation.

An objective of the present invention is to provide a novel bacterial strain and compositions thereof which can be used in medicine, especially in the treatment and/or prevention of inflammation, such as in the oral cavity, in particular in the treatment and/or prevention of gingivitis and/or periodontitis.

A further objective of the present invention is to provide a novel bacterial strain and compositions thereof which are capable of reducing or inhibiting the release of one or more inflammatory factors such as interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-κB.

The objective of the present invention is met by providing *Lactobacillus plantarum* strain GOS 42, which was deposited by Probi AB of Solvegatan 41, 22370 Lund, Sweden at Leibniz Institute DSMZ-German Collection of Microorganisms and Cell Cultures, Inhoffenstr. 7 B, D-38124 Braunschweig, in accordance with the requirements of the Budapest Treaty on 2 Sep. 2015 and has received the deposit accession number DSM 32131 and compositions thereof.

The strain of the invention was isolated from the saliva of healthy human volunteers and selected from amongst over 50 candidate probiotic strains including strains of *Bacillus subtilis, Bifidobacterium animalis, Bifidobacterium bifidum, Bifdobacterium longum, Bifidobacterium breve, Bifidobacterium lactis, Lactobacillus acidophilus, Lactobacillus casei, Lactobacillus LAFTI, Lactobacillus plantarum, Lactobacillus reuteri, Lactobacillus rhamnosus, Lactobacillus paracasei, Lactobacillus bulgaricus, Lactobacillus gasseri, Lactobacillus fermentum, Lactobacillus brevis, Lactobacillus cellobiosus, Lactobacillus salivarius, Streptococcus thermophilus* and *Lactococcus lactis*.

By extensive screenings, the bacterial strain according to the invention has been identified to exhibit distinct modulating activity mostly in an inhibitive manner against the release of certain pro-inflammatory factors while, at the same time, does not or only negligibly enhance the release of other pro-inflammatory factors. The present invention now allows for an optimized use of a probiotic bacterial strain for the prevention and/or treatment of inflammatory conditions, especially those occuring in the oral cavity, which has not been possible before.

As explained above, the colonization of the oral mucosa by disease-associated bacteria and the formation of plaque can tip the microbial balance in the oral cavity towards an accumulation of detrimental microorganisms, which is also referred to as dysbiosis. Therefore, the microorganism for use in the prevention and/or treatment of inflammation in the oral cavity according to the invention includes the use in the prevention and/or treatment of plaque and plaques associated diseases and advantageously aides to avoid oral dysbiosis by balancing the mouth flora towards a healthy state.

In a preferred embodiment of the present invention the microorganism described above is attenuated or dead, preferably heat-inactivated, ideally by incubation for 2 to 8 minutes at a temperature between 70 and 100° C.

In the studies described below, it has been demonstrated that the microorganism according to the invention can provide inhibitory effects on the release of pro-inflammatory factors even in an inactivated state. Therefore it is also possible to use the novel strain when it is dead or heat-inactivated. Remarkably, heat inactivated strains may show the same or even slightly enhanced anti-inflammatory activity towards certain factors.

In one aspect, the present invention relates to the microorganism recited above for use as anti-inflammatory agent, especially for reducing or inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-κB.

According to another aspect of the present invention, fragments of the novel strain of microorganism as defined in any of the aspects described above may be used in the treatment and/or prevention of inflammation, especially in the oral cavity, and preferably in the treatment and/or prevention of gingivitis and/or periodontitis.

It may not be necessary to use whole cells of the novel strain of the invention as mixtures comprising only fragments (e.g. debris of degraded cells) of the microorganisms are sufficient to provide the inventive effects.

In a further aspect, the present invention also relates to a pharmaceutical composition, comprising *Lactobacillus plantarum* GOS 42 or fragments thereof and a pharmaceutically acceptable carrier, exipient and/or diluent. The total amount of the microorganism or fragments thereof is preferably sufficient for treating and/or preventing inflammation especially in the oral cavity, preferably for treating and/or preventing gingivitis and/or periodontitis. Preferably the total amount of the microorganism or fragments thereof is in the range from 0.01 to 100%, more preferably in the range from 0.1 to 50%, most preferably in the range from 1 to 10%, in each case with respect to the total weight of the composition, and/or wherein the total amount of the microorganism(s) or the fragments thereof is in the range from $1 \times 10^3$ to $1 \times 10^{11}$ colony forming units (CFU), more preferably in the range from $1 \times 10^5$ to $1 \times 10^{10}$ CFU, and ideally from $1 \times 10^8$ to $1 \times 10^9$ CFU.

In a preferred embodiment, the microorganism (bacteria) of the invention is present in a composition at a concentration of approximately $1 \times 10^3$ to $1 \times 10^{14}$ colony forming units (CFU) per gram, preferably approximately $1 \times 10^5$ to $1 \times 10^{12}$ CFU/gram, whereas in other embodiments the concentrations are approximately $1 \times 10^9$ to $1 \times 10^{13}$ CFU/gram, approximately $1 \times 10^5$ to $1 \times 10^7$ CFU/gram, or approximately $1 \times 10^8$ to $1 \times 10^9$ CFU/gram. However, it will be appreciated that is the overall CFU rather than the concentration which is most important.

In one embodiment the bacteria of the invention is in a pharmaceutically acceptable carrier or food product suitable for oral administration to mammal, preferably as a powdered food supplement, a pelletized formulation, or a liquid formulation. The mammal is preferably a human.

The skilled person is aware that the probiotic organism used in a composition or product according to the invention represent biologic material the activity of which may vary with the batch and depends also on the production or processing method. Therefore, the suitable amount can be adjusted accordingly within the given range.

Furthermore, the present invention relates to a composition or product as described above for use in medicine, preferably in the treatment and/or prevention of inflammation, especially in the oral cavity, and most preferably for use in the treatment and/or prevention of gingivitis and/or periodontitis.

A composition according to the invention may further comprise one or more components selected from the group consisting of carriers, excipients or further active ingredients such as, for example, active agents from the group of non-steroidal antiphlogistics, antibiotics, steroids, anti-TNF-alpha antibodies or other biotechnologically produced active agents and/or substances as well as analgetics, dexpanthenol, prednisolon, polyvidon iodide, chlorhexidine-bis-D-gluconate, hexetidine, benzydamine HCl, lidocaine, benzocaine, macrogol lauryl ether, benzocaine in combination with cetidyl pyridinium chloride or macrogol lauryl ether in combination with protein free hemodialysate from calf blood, as well as for example fillers (e.g. cellulose, calcium carbonate), plasticizer or flow improves (e.g. talcum, magnesium stearate), coatings (e.g. polyvinyl acetate phtalate, hydroxyl propyl methyl cellulose phtalate), disintegrants (e.g. starch, cross-linking polyvinyl pyrrolidone), softener (e.g. triethyl citrate, dibutyl phthalate) substances for granulation (lactose, gelatin), retardation (e.g. poly (meth)acrylic acid methyl/ethyl/2-trimethyl aminomethyl ester copolymerizates in dispersion, vinyl acetate/crotonic acid copolymerizates), compaction (e.g. microcrystalline cellulose, lactose), solvents, suspending or dispersing agents (e.g. water, ethanol), emulsifiers (e.g. cetyl alcohol, lecithin), substances for modifying the rheological properties (silica, sodium alginate), substances for microbial stabilization (e.g. benzalkonium chloride, potassium sorbate), preservatives and antioxidants (e.g. DL-alpha-tocopherol, ascorbic acid) substances for modifying pH (lactic acid, citric acid), blowing agents or inert gases (e.g. fluorinated chlorinated hydrocarbons, carbon dioxide), dyes (iron oxide, titanium oxide), basic ingredients for ointment (e.g. paraffines, bees wax) and others as described in the literature (e.g. in Schmidt, Christin. Wirk- und Hilfsstoffe für Rezeptur, Defektur und Großherstellung. 1999; Wissenschaftliche Verlagsgesellschaft mbH Stuttgart oder Bauer, Frömming Führer. Lehrbuch der Pharmazeutischen Technologie. 8. Auflage, 2006. Wissenschaftliche Verlagsgesellschaft mbH Stuttgart).

A composition or product according to the present invention may also be coated or encapsulated.

Encapsulation of a composition according to the invention may have the advantage of allowing a controlled release, for example upon contact with water, or a continuous release over an extended period of time. Moreover, the composition may be protected from degradation improving the shelf life of the product. Methods for encapsulation of active ingredients are well known in the art and a number of encapsulation materials as well as methods how to apply them to a composition according to specific requirements are available.

Furthermore, a composition or product according to the invention may be in the form of a solution, suspension, emulsion, tablets, granules, powder or capsules.

The composition or product according to the invention may be selected form the group consisting of toothpaste, tooth gel, tooth powder, tooth cleaning liquid, tooth cleaning foam, mouth wash, mouth spray, dental floss, chewing gum and lozenges.

Such compositions or products may contain abrasive systems (abrasive and/or polishing components) such as silicates, calcium carbonate, calcium phosphate, aluminum oxide and/or hydroxyl apatite, surfactants such as e.g. sodium lauryl sulfate, sodium lauryl sarcosinate and/or cocamidopropyl betaine, humectants such as glycerol and/or sorbitol, thickening agents, e.g. carboxy methyl cellulose, poly ethylene glycols, carrageenans and/or Laponite®, sweeteners such as saccharine, aroma and taste correcting agents for unpleasant taste impressions, taste modifying substances (e.g. inositol phosphate, nucleotides, e.g. guanosine monophosphate, adenosine monophosphate or other substances, e.g. sodium glutamate or 2-phenoxy propionic acid), cooling agents such as menthol derivates (e.g. L-mentyl lactate, L-menthyl alkyl carbonate, menthone ketals), icilin and icilin derivates, stabilizers and active agents such as sodium fluoride, sodium monofluoro phosphate, tin difluoride, quarternary ammonium fluorides, zinc citrate, zinc sulfate, tin pyrophosphate, tin dichloride, mixtures of different pyrophosphates, triclosane, cetyl pyridinium chloride, aluminum lactate, potassium citrate, potassium nitrate, potassium chloride, strontium chloride, hydrogen peroxide, aroma substances, sodium bicarbonate and/or smell correcting agents.

Chewing gums or dental care chewing gums may comprise a chewing gum base comprising elastomers, e.g. polyvinyl acetate (PVA), polyethylene, (low or medium molecular) polyiso butane (PIB), polybutadiene, isobutene/isoprene copolymers, polyvinyl ethyl ether (PVE), polyvinyl butyl ether, copolymers of vinyl esters and vinyl ethers, styrene/butadiene copolymers (SBR) or vinyl elastomers, e.g. based on vinyl acetate/vinyl laurate, vinyl acetate/vinyl stearate or ethylene/vinyl acetate and mixtures of the mentioned elastomers as e.g. example described EP 0 242 325, U.S. Pat. Nos. 4,518,615, 5,093,136, 5,266,336 5,601,858 or 6,986,709. Additionally chewing gum bases may contain further ingredients, e.g. (mineral) filers, e.g. calcium carbonate, titanium dioxide, silicone dioxide, talcum, aluminum oxide, dicalcium phosphate, tricalcium phosphate, magnesium hydroxide and mixtures thereof, plasticisers (e.g. lanolin, stearic acid, sodium stearate, ethyl acetate, diacetin (glycerol diacetate), triacetin (glycerol triacetate) and trietyhl citrate), emulsifiers (e.g. phosphatides, such as lecithin and mono and diglycerides of fatty acids, e.g. glycerol monostearate), antioxidants, waxes (e.g. paraffine waxes, candelilla waxes, carnauba waxes, microcrystalline waxes and polyethylene waxes), fats or fatty oils (e.g. hardened (hydrogenated) plant or animal fats) and mono, di or triglycerides.

The following examples are added to illustrate the present invention without being intended to limit the scope.

Example 1: Establishing the Cultivation and Handling of Probiotic Strains

The strain of the invention was selected from amongst over 50 candidate probiotic strains including strains of *Bacillus subtilis, Bifidobacterium animalis, Bifidobacterium bifidum, Bifdobacterium longum, Bifidobacterium breve, Bifidobacterium lactis, Lactobacillus acidophilus, Lactobacillus casei, Lactobacillus* LAFTI, *Lactobacillus plantarum, Lactobacillus reuteri, Lactobacillus rhamnosus, Lactobacillus paracasei, Lactobacillus bulgaricus, Lactobacillus gasseri, Lactobacillus fermentum, Lactobacillus brevis, Lactobacillus cellobiosus, Lactobacillus salivarius, Streptococcus thermophilus* and *Lactococcus lactis*.

In order to identify the optimal growth conditions and points of harvest and to determine the colony forming units (CFU) for the probiotic bacteria to be screened, first the log phase and the end of the growth phase were determined.
Bacterial Growth The frozen (−80° C.) pro-biotic stocks were thawed over-night at 4° C. and 6 ml of sterile 9% NaCl solution added to the 1.2 ml of bacteria at the next morning. The samples were centrifuged (5 min, 5000 rpm), the supernatant discarded, the pellet washed with 8 ml 9% NaCl and again centrifuged for 5 min at 5000 rpm. The pellet was then resuspended in 1.2 ml 9% NaCl and 1 ml of the sample added to 50 ml 37° C. warm media (MRS Bouillon, Carl Roth K G, Karlsruhe) and incubated at 37° C. The incubations were performed in a 50 ml sterile polypropylen tube (Greiner) and probes were harvested at different time points to evaluate the growth curve.

OD-Determination

For determination of OD, 500 µl of the bacterial suspension were removed and diluted in 1 ml MRS Bouillon in a 1.5 ml-PS-cuvette (Brand). OD-determination was performed at 600 nm (ThermoScientific, Helios Epsilon) 1.5 ml MRS Bouillon were used as blanc.

Determination of CFU

For determination of CFU, bacteria were diluted (1:10,000,000, 1:50,000,000 and 1:100,000,000), plated on MRS-agar-plates (MRS Agar, X924, Carl Roth) and incubated for 2 days at 37° C. The grown colonies were then counted and the CFU was calculated.

The bacteria approached the log phase right from the beginning until 7 to 8 hours when they start to reach the plateau phase. The amount of bacteria to be seeded does not change the shape of the curve. 5 hours were chosen as the point at the steepest growing phase to harvest the bacteria in the log phase and 7 hours to harvest them at the end of the log phase.

Example 2: Establishing the Stimulation of Human Monocytes with Probiotics

The stimulation of the monocyte cell cultures with the novel probiotics strain was established by using the strains obtained as powder. First, several application forms such as using the grown bacteria (picked from the log-phase), the supernatant of the grown bacterial cultures, direct application of the dissolved powder and powder supernatant were tested. According to the results, the bacteria at the end of the log phase were tested this with two batches of the frozen strain. Instead of using the supernatants, heat inactivation of these two strains was established and compared the inactivated bacteria with the activated bacteria.

Measurement of Cytokine; MMP-9 and PGE2 in Primary Human Monocytes

Human primary monocytes were isolated from buffy coats of healthy human blood donors. Cells were seeded in 24-well-plates for ELISA experiments. Cells were incubated with LPS for 24 h. The probiotics (5 doses) were added 30 min before LPS treatment. After 24 h, supernatants were removed, centrifuged and investigated for IL-1beta, TNFalpha, IL-6, IL-8, MMP-9, isoprostane-8 and $PGE_2$ concentrations in ElAs (PGE2, from AssayDesign, isoprostane, from Cayman) or ELISAs (all cytokines, Immunotools, MMP-9, GE Healthcare) using manufacturer's protocol. Each dose was investigated 2-3 times in two buffy coats from 2 different donors.

First, different types of probiotic lyophilized powder preparations for the stimulation of human monocytes were tested.

The probiotics were harvested and then centrifuged. The cells were dissolved in fresh media and applied to the human monocytes.

The monocytes were then incubated with the probiotics for 30 minutes, then LPS was added and after 24 hours the supernatant removed and use for the determination of the inflammatory parameters.

Example 3: Testing of Heat Inactivated Strains

Establishment of Heat Inactivation

Heat inactivation was established for two batches. At the end of the bacterial growth log phase, an aliquot of the bacterial suspension was removed, added to a fresh 50 ml tube and incubated for 5 min at 80° C. in a water bath. 5 minutes at 80° C. inactivated the bacteria and thus stopped their growth.

Testing the heat inactivated batches of the strain, it was found that the enhancing effects on IL-1 and TNF were not affected by heat treatment Furthermore, heat activation did not or only slightly affect PGE2 inhibition by both strains.

Example 4: Screening of the Probiotics on Human Monocytes and Effects on NF-kappaB Activation Various probiotic strains were screened in their activated and attenuated (heat-inactivated form) on LPS-induced human primary monocytes (determining IL-1beta, IL-6, IL-8, TNFalpha, PGE2, 8-isoprostane, and MMP-9.

A typical anti-inflammatory pattern of the novel strain according to Examples 1-4 is given in FIGS. 1A-1F.

The experiments to test effects on NF-kappaB activation induced by TNFin NIH-3T3 fibroblasts were done in a fibroblast cell line that contained stably transfected the Luciferase gene drive by a NF-kappaB dependent promoter. The cells were stimulated with TNF in the presence or absence of the probiotics. After 6 h of stimulation the cells were lysed and the luciferase activity measured in a Luminometer.

Example 5: Screening of Selected Probiotics on Human Gingival Fibroblasts

The selected strain of the invention was applied to human gingival fibroblasts. The fibroblast cultures were maintained as described in the manufacturer's protocol. Prior to stimulation, cells are seeded in 24-well plates for ELISA experiments. Cells were incubated without (unstimulated control) or with IL-1beta for 24 h. The probiotics (5 doses, depending on the outcome of screening assays) are added 30 min before IL-1 treatment. After 24 h, supernatants were removed, centrifuged and investigated for IL-6, IL-8, isoprostane, and PGE2 concentrations in ElA (PGE2, from AssayDesign, isoprostane form Cayman) or ELISA (IL-6, IL-8, Immunotools), using manufacturer's protocol. Each dose was investigated at least 2-3 times. The strains showed some IL-6 inhibiting effects.

Figure 2:
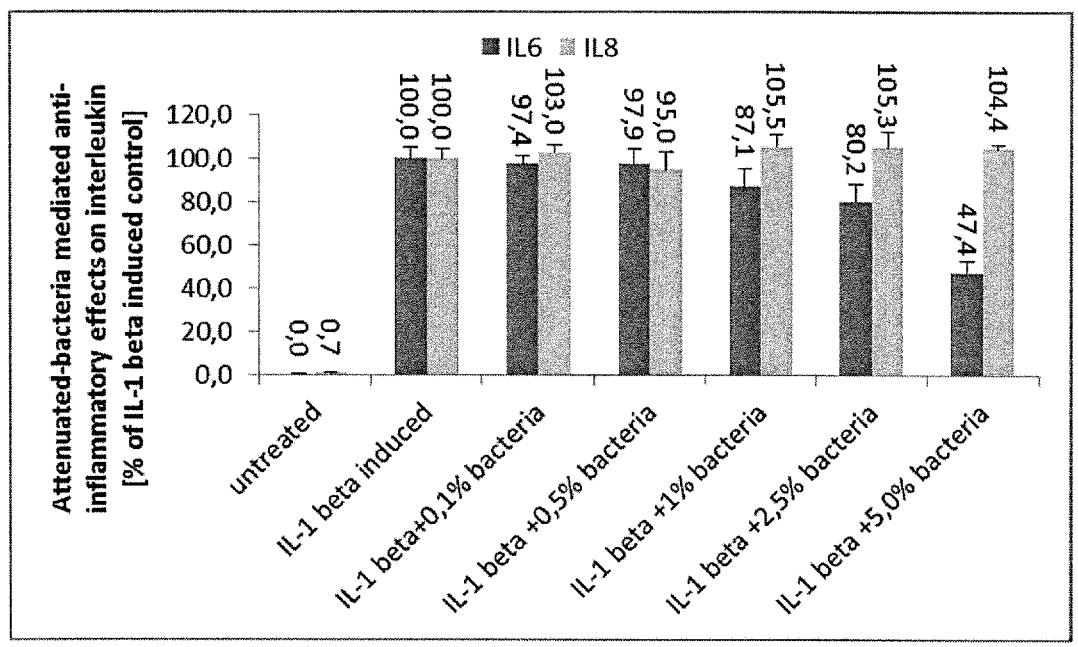
FIG. 2 shows the anti-Inflammatory effects of *Lactobacillus plantarum* GOS 42 (DSM 32131) in attenuated form on interleukin in human gingival fibroblasts. The left column refers to interleukin 6, the right column to interleukin 8.

An anti-inflammatory pattern of the strain according to Example 5 is given in FIG. 2.

Example 6: Probiotic Lozenge or Comprimate

|   |   |   |   | Isomalt Comprimates | |
|---|---|---|---|---|---|
| No | Block | Ingredients | Placebo | Probiotic only | +Flavor |
| 1 | A | Magnesium Stearate | 1.800% | 1.800% | 1.800% |
| 2 |   | Acesulfam | 0.050% | 0.050% | 0.050% |
| 3 |   | Sucralose | 0.025% | 0.025% | 0.025% |
| 4 |   | Probiotic Material |   | 1.000% | 1.000% |
| 5 |   | Flavor (e.g. 134229 Optamint Peppermint s/d) |   |   | 0.500% |

-continued

| No | Block | Ingredients | Isomalt Comprimates | | |
|----|-------|-------------|---------|------------------|---------|
|    |       |             | Placebo | Probiotic only | +Flavor |
| 6  | B     | Isomalt     | 98.125% | 97.125%        | 96.625% |
|    |       | Sum total   | 100.00% | 100.00%        | 100.00% |

Production Method:
  components 1 and 6 are dried in a vacuum compartment drier at 50° C. and a pressure of max. 10 mbar for 16 hours
  all components are weight out exactly
components 1, 2, 3, 4 and 5 combined and thoroughly mixed (block A). The probiotic material is applied in lyophilized form having an activity of about $10^5$ to $10^{12}$ colony forming units (CFU) per gram.
  block A is subsequently added to component 6 and mixed thoroughly for 5 minutes
  the powder mixture is pressed into tablets in a tablet press EK0 (Korsch AG, Berlin) at an adjusted pressure of 15-20 kN
target parameters:
  tablet diameter: 20 mm
  tablet weight: 2.0 g
  storage at RT in sealed aluminum sachets. Per 5 lozenges 1 g of desiccant is used for dehumidification (activated by 3 h storage at 105° C. in a vacuum compartment drier)

Example 7: Powder Dentifrice

| No | Block | Ingredients | Toothpowder | | |
|----|-------|-------------|---------|----------------|---------|
|    |       |             | Placebo | Probiotic only | +Flavor |
| 1  | A     | Magnesium Carbonate | 3.00% | 3.00% | 3.00% |
| 2  |       | Sodium Bicarbonate | 2.00% | 2.00% | 2.00% |
| 3  |       | Sodium Fluoride | 0.25% | 0.25% | 0.25% |
| 4  |       | Sodium Saccharin | 0.60% | 0.60% | 0.60% |
| 5  | B     | Probiotic Material |  | 4.00% | 4.00% |
| 6  |       | Flavor (e.g. 134229 Optamint Peppermint s/d) |  |  | 2.00% |
| 7  | C     | Calcium carbonate | 94.15% | 90.15% | 88.15% |
|    |       | Sum total   | 100.00% | 100.00% | 100.00% |

Production Method:
  component 7 is dried in a vacuum compartment drier at 50° C. and a pressure of max. 10 mbar for 16 hours
  all components are weight out exactly
  components 1, 2, 3 and 4 are combined and thoroughly mixed together (block A)
  components 5 and 6 are, if necessary, combined and thoroughly mixed (block B). The probiotic material is applied in lyophilized form having an activity of about $10^5$ to $10^{12}$ colony forming units (CFU) per gram.
  blocks A and B are subsequently combined and thoroughly mixed together
  the mixture is added to component 7 and mixed thoroughly for 5 minutes
  the powder mixture is made up into portions of 0.5 g each storage at RT together with 1 g of desiccant per portion (activated by 3 h storage at 105° C. in a vacuum compartment drier) in sealed aluminum sachets Example 8: Powder Dentifrice

| No | Block | Ingredients | Toothpaste tablets |
|----|-------|-------------|--------------------|
| 1  | A     | Magnesium Carbonate | 3.00% |
| 2  |       | Sodium Bicarbonate | 2.00% |
| 3  |       | Sodium Fluoride | 0.25% |
| 4  |       | Sodium Saccharin | 0.60% |
| 5  |       | Sodium Laurylsulphate | 0.50% |
| 6  |       | Magnesium Stearate | 1.00% |
| 7  | B     | Flavor (e.g. 134229 Optamint Peppermint s/d) | 2.00% |
| 8  |       | Probiotic Material | 6.67% |
| 9  | C     | Calcium Carbonate | 17.00% |
| 10 |       | Microcristalline Cellulose | 66.98% |
|    |       | Sum total   | 100.00% |

Production Method:
  components 6, 9 and 10 are dried in a vacuum compartment drier at 50° C. and a pressure of max. 10 mbar for 16 hours.
  all components are weight out exactly
  components 1, 2, 3, 4, 5 and 6 are combined and thoroughly mixed together (block A)
  components 1 and 8 are combined and thoroughly mixed together (block B). The probiotic material is applied in lyophilized form having an activity of about $10^5$ to $10^{12}$ colony forming units (CFU) per gram.
  blocks A and B are subsequently combined and thoroughly mixed together
  components 9 and 10 are combined and thoroughly mixed together (block C)
  the two mixtures (Block A/B and Block C) are combined and mixed thoroughly for 5 minutes
  the powder mixture is pressed into tablets in a tablet press EK0 (Korsch AG, Berlin) at an adjusted pressure of 15-20 kN
target parameters
  tablet diameter: 9 mm
  tablet weight: 0.3 g
  storage at RT in sealed aluminum sachets. Per 3 tablets 1 g of desiccant is used for dehumidification (activated by 3 h storage at 105° C. in a vacuum compartment drier)

Example 9: Chewing Gum

| No | Ingredients | Chewing gum with Vegetable Oil, Probiotics in Flavor | Chewing gum with Vegetable Oil, Probiotics in Oil |
|----|-------------|------------------|------------------|
| 1  | Gum Base (e.g. Geminis T) | 30.00% Block A | 30.00% Block A |
| 2  | Isomalt (here: Isomalt ST-PF) | 65.00% Block B | 65.00% Block B |

-continued

| No | Ingredients | Chewing gum with Vegetable Oil, Probiotics in Flavor | Chewing gum with Vegetable Oil, Probiotics in Oil |
|---|---|---|---|
| 3 | Sucralose coated (10% in wax) | 1.00% | 1.00% |
| 4 | Deoiled Soy Lecithin (here: Emulpur IP) | 0.30% | 0.30% |
| 5 | Vegetable Oil - Triglyceride | 1.60% Block C | 1.60% Block C |
| 6 | Probiotic Material | 0.80% Block D | 0.80% |
| 7 | Flavor (e.g. 203191 Optamint Peppermint) | 1.30% | 1.30% Block D |

Production Method:
  component 2 is dried in a vacuum compartment drier at 50° C. and a pressure of max. 10 mbar for 16 hours
  all components are weight out exactly
  component 1 is tempered to 45-59° C. in a chewing gum lab-kneader with the heating kneaded until a homogenous mass is obtained. The heating is on during the whole mixing process
  components 2, 3 and 4 are added subsequently and kneaded until the mixture is homogenous and no powder is visible anymore
  according to the formula component 6 is either worked into component 5 (block C) or component 7 (block D). The probiotic material is applied in lyophilized form having an activity of about $10^5$ to $10^{12}$ colony forming units (CFU) per gram. The components are mixed until an even suspension is obtained.
  First, block C is added to the chewing gum mass and kneaded again until a homogenous mass is obtained.
  Last, block D is processed accordingly. After addition the composition has to be kneaded until an even chewing gum mass is obtained.
  the mass is taken out of the mixer and is formed into mini-sticks by an embossing roller using the embossing set "slabs"
  storage at RT in sealed aluminum sachets. Per 7 chewing gums 1 g of desiccant is used for dehumidification (activated by 3 h storage at 105° C. in a vacuum compartment drier)

Example 10: Probiotic Beadlets

Production Method:
  Production of the calcium chloride bath for precipitation of the alginate beadlets:
    a 2% calcium chloride solution is produces from distilled water and calcium chloride. Care has to be taken that the $CaCl_2$ is completely dissolved.
  Production of the alginate solution (instead of alginate also pectin or gellan gum may be used):
    in a reaction vessel with a stirrer and which is suitable to the batch size, water is provided
    the stirrer is turned on and, while stirring at a high level, the respective amounts of alginate, gum arabicum, wheat fiber and probiotic, as well as the optionally required gellan gum are added
    the mixture is heated to 80° C. while stirring and kept at this temperature for 5 minutes—during this step the gel forming components are dissolved
    afterwards, the heating is turned off and the hot gel solution is further stirred for at least 30 minutes until it is free of lumps
    subsequently, the solution is cooled by refrigeration to 39-43° C. while stirring
    in a further vessel, the aroma and the dye are provided if required and thoroughly mixed In case no aroma is used, the dye is mixed with glycerol
    when the dye dispersion is mixed homogenously, it is added to the batch vessel with the alginate solution. The mixing vessel is washed several times with approx. 10% of the amount of alginate solution used of water and added to the dispersion
    the alginate dispersion is stirred further for at least 5 minutes.
  Subsequently, the batch is stirred for further at least 15 minutes at a low speed to remove potentially present air.

| components | probiotic beadlets with low load, without aroma, with dye, with gellan gum wt. % | probiotic beadlets with low load, with aroma, with dye, with gellan gum wt. % | probiotic beadlets with high load, without aroma, without dye, without gellan gum, high water content wt. % | probiotic beadlets with high load, without aroma, without dye, without gellan gum, low water content wt. % |
|---|---|---|---|---|
| Alginate | 1.75 | 1.65 | 1.44 | 1.57 |
| Gummi Arabicum | 1.25 | 1.18 | 0.60 | 0.65 |
| Wheat fiber | 1.125 | 1.06 | 0.52 | 0.57 |
| Dye | 0.0125 | 0.018 | — | — |
| Aroma | — | 1.41 | — | — |
| Glycerol | 0.1875 | — | — | — |
| probiotic | 1.125 | 1.35 | 7.20 | 7.83 |
| Gellan Gum | 0.0625 | 0.059 | — | — |
| Water | Add to 100 | Add to 100 | Add to 100 | Add to 100 |
| load | approx. 20% | approx. 20% | approx. 74% | approx. 74% |

Dripping of the Alginate Solution into the Calcium Chloride Solution for Precipitation of the Beadlets:

the alginate dispersion is moved to a tightly sealable pressure stable reaction vessel having two outlets. At one outlet pressurized air is applied. The second outlet leads to the nozzles of the dripping unit via a tube.

the reaction vessel is tempered over a heating plate so that the alginate solution reaches a temperature of approx. 45° C. The solution is slightly stirred with a magnet stirrer.

after application of pressure to the reaction vessel, alginate solution is pressed towards the nozzles, which are set to oscillation by an oscillator. By adaption of pressure and the frequency of the oscillator, the size of the resulting drops at the tips of nozzles may be adjusted.

The drops of alginate solution forming at the tips of the nozzles fall into a collection vessel in the form of a funnel in which the calcium chloride solution prepared at the beginning circulates.

the cured alginate beadlets pass with the calcium chloride solution through the funnel and are collected in a sieve, the collected calcium chloride solution is pumped back into the funnel below the dripping unit and thus recycled.

the beadlets are dried in an Aeromatic flowbed-drier at an supply air temperature of 80° C. until an exhaust air temperature of 45° C. is reached

The invention claimed is:

1. A composition comprising:
   (a) the microorganism *Lactobacillus plantarum* GOS 42 (DSM 32131); and
   (b) a carrier, excipient and/or diluent.

2. The composition as claimed in claim 1 wherein the composition is a pharmaceutical composition.

3. The composition of claim 1, wherein the total amount of the microorganism is in the range from 0.01 to 100% with respect to the total weight of the composition, and/or wherein the total amount of the microorganism is in the range from $1 \times 10^3$ to $1 \times 10^{11}$ colony forming units (CFU).

4. The composition as claimed in claim 3 wherein the total amount of microorganism is in the range of from 0.1 to 50% with respect to the total weight of the composition; and/or the total amount of the microorganism is in the range of from $1 \times 10^5$ to $1 \times 10^{10}$ CFU.

5. The composition as claimed in claim 4 wherein the total amount of the microorganism is in the range of from 1 to 10% with respect to the total weight of the composition; and/or wherein the total amount of the microorganism is in the range of from $1 \times 10^8$ to $1 \times 10^9$ CFU.

6. The composition according to claim 1, wherein the composition is coated or encapsulated.

7. The composition according to claim 1, wherein the composition is in the form of a solution, suspension, emulsion, tablet, granule, powder or capsule.

8. The composition according to claim 1, wherein the composition is selected from the group consisting of toothpaste, tooth gel, tooth powder, tooth cleaning liquid, tooth cleaning foam, mouth wash, mouth spray, dental floss, chewing gum and lozenge.

9. The composition according to claim 1 wherein the composition is in the form of an animal food and/or drink component.

10. The composition according to claim 1, wherein the microorganism is present as vegetative cells and/or spores.

11. The composition according to claim 1, wherein the microorganism is attenuated or dead.

12. A method of treating or preventing inflammation, the method comprising administering to a subject in need thereof the composition according to claim 1.

13. The method of claim 12, wherein the method is for reducing and/or inhibiting the release of one or more inflammatory factors selected from the group consisting of interleukin 1 (IL-1), interleukin 6 (IL-6), interleukin 8 (IL-8), tumor necrosis factor (TNF), prostaglandin E2 (PGE2), isoprostanes, matrix metallopeptidase 9 (MMP9) and NF-κB.

* * * * *